United States Patent [19]

Minh et al.

[11] Patent Number: 4,499,115

[45] Date of Patent: Feb. 12, 1985

[54] ANTIOXIDANT BENZODIOXOLE COMPOUND

[75] Inventors: Thi H. Minh, Kingsford; Edward R. Cole, Turramurra; George Crank, Sdyney, all of Australia

[73] Assignee: Unisearch Limited, Kensington, Australia

[21] Appl. No.: 454,883

[22] Filed: Dec. 30, 1982

Related U.S. Application Data

[63] Continuation of Ser. No. 222,986, Jan. 7, 1981, abandoned.

[30] Foreign Application Priority Data

Jan. 7, 1980 [AU] Australia .............................. PE1920

[51] Int. Cl.³ ...................... A23D 5/04; C07D 317/06
[52] U.S. Cl. .................................... 426/546; 549/437; 426/601
[58] Field of Search ................ 260/340.5 R; 549/437; 426/541, 546, 610

[56] References Cited

U.S. PATENT DOCUMENTS

| | | | |
|---|---|---|---|
| 2,124,749 | 7/1938 | Salzberg ............................ | 426/546 |
| 2,837,534 | 6/1958 | Tracy ............................ | 260/340.5 R |
| 3,443,970 | 5/1969 | Wolf et al. ............................ | 426/546 |
| 3,922,285 | 11/1975 | Leimgruber et al. ........ | 260/340.5 R |
| 3,948,952 | 4/1976 | Gates et al. .................. | 260/340.5 R |
| 3,969,416 | 7/1976 | Shaw ............................ | 260/340.5 R |

OTHER PUBLICATIONS

Cole et al., "Antioxidant Properties of Synthetic 5-Hydroxy-1,3-benzodioxole Derivatives", *J. Agric Food Chem.*, vol. 30, ©1982, pp. 719-724.

*Primary Examiner*—Robert Yoncoskie
*Assistant Examiner*—Elizabeth C. Weimar
*Attorney, Agent, or Firm*—Holman & Stern

[57] ABSTRACT

Novel antioxidant compounds for use in foodstuffs containing oils or fats are described which comprise benzodioxole compounds having the structure

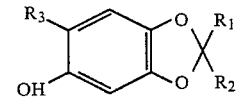

wherein
$R_1$ is a hydrogen atom or an alkyl group or an aryl group,
$R_2$ is an alkyl group or an aryl group,
or $R_1$ and $R_2$ together form a cyclo alkyl group, and
$R_3$ is a hydrogen atom or an hydroxyl group.

9 Claims, 1 Drawing Figure

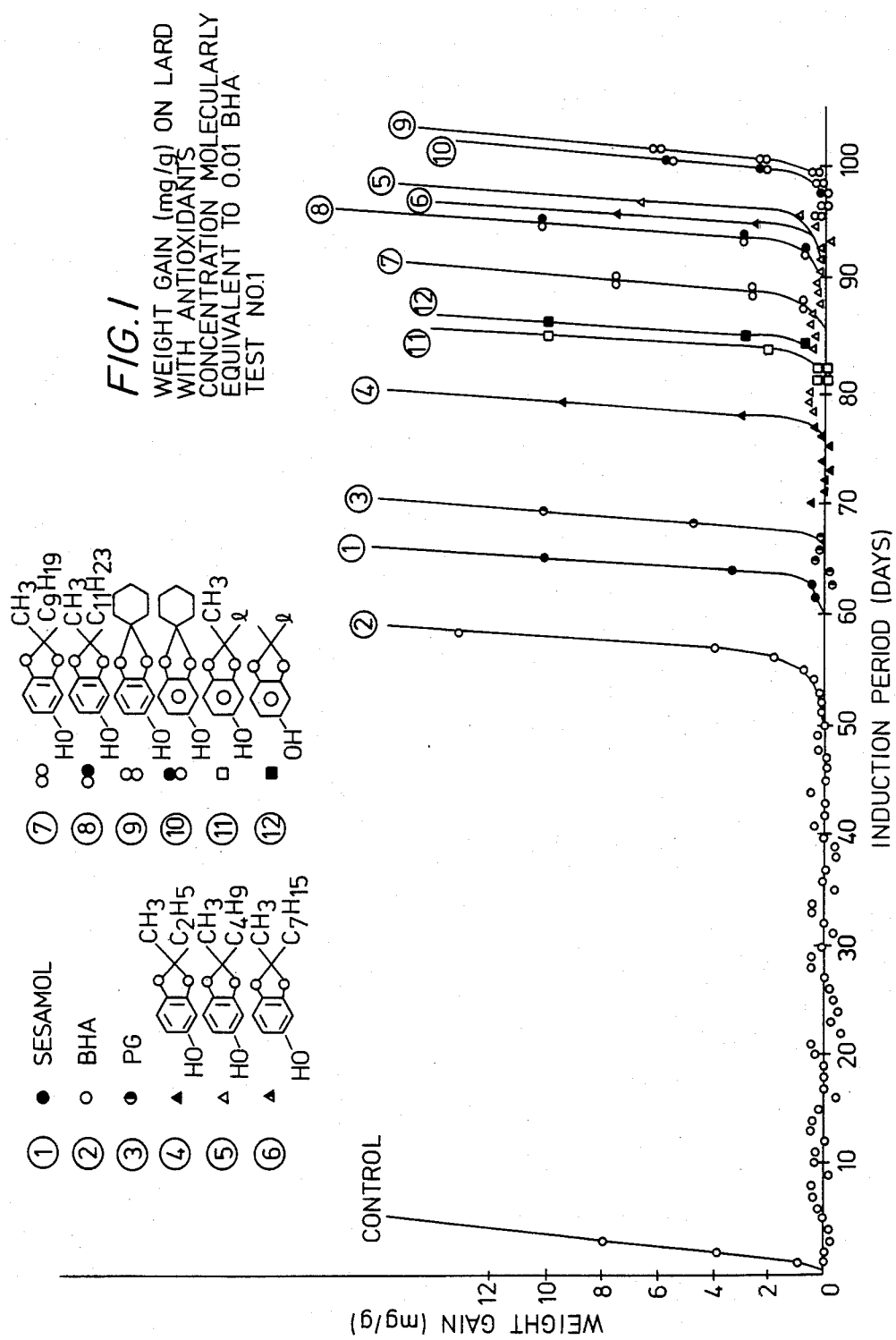

ANTIOXIDANT BENZODIOXOLE COMPOUND

This is a continuation of application Ser. No. 222,986, filed Jan. 7, 1981 which in turn is now abandoned.

The present invention relates to novel benzodioxole compounds, to their formation, and to their use as antioxidants.

The present invention consists in benzodioxole compounds having the structure

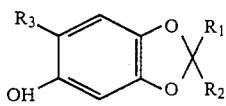

wherein $R_1$ is a hydrogen atom or an alkyl group or an aryl group;

$R_2$ is an alkyl group or an aryl group;

or $R_1$ and $R_2$ together form a cyclo alkyl group; and $R_3$ is a hydrogen atom or an hydroxyl group The present invention further consists in a method for the formation of benzodioxole compounds according to this invention comprising reacting catechol with an aldehyde or ketone having the formula

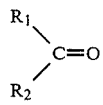

wherein $R_1$ and $R_2$ have the meanings set out above, in the presence of hydrogen ions, reacting the substituted benzodioxole so formed with lead tetra-acetate, respectively hydrolysing or reducing the acetoxy or oxo-substituted benzodioxole compound so formed; and recovering the desired hydroxy substituted benzodioxole compound.

The compounds according to the present invention have been found to be highly effective antioxidants and in particular to be useful as antioxidants for use in foodstuffs. Amounts of from 0.1% to 0.001% by weight have been found to be effective.

In the method for the formation of the compounds according to the present invention the reaction between the catechol and the aldehyde or ketone must take place in the presence of hydrogen ions. These hydrogen ions are preferably provided by a strong acid such as sulphuric acid, phosphoric acid or p-toluenesulphonic acid.

The hydrolysis of the acetoxy substituted compound to yield the hydroxy substituted compound is preferably carried out under alkaline conditions and is followed by acidification.

BRIEF DESCRIPTION OF THE DRAWINGS

FIG. 1 is a graphic representation of the weight gain (mg/g) on lard at various days with and without antioxidants concentration molecularly equivalent to 0.01 BHA.

The following examples illustrate the first stage of the method according to this invention wherein catechol is reacted with an aldehyde or ketone to produce a substituted benzodioxole illustrated by the diagrammatic representations:

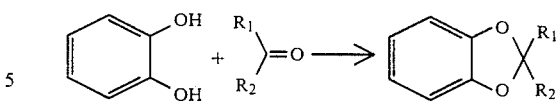

wherein $R_1$ and $R_2$ have the meanings given above.

EXAMPLE I

General Methods.

Reagent grade catechol (Merck) was purified by recrystallization. The purity of aldehydes and ketones was checked by gas-liquid chromatography.

(a) 2-Methyl-2-n-pentyl-1,3-benzodioxole: Catechol (33 g) and methyl-n-pentyl ketone (34.2 g 1 equivalent) with p-toluenesulphonic acid (10 mg) were heated under reflux in toluene (300 ml) for 10 hours (in a Dean & Stark apparatus). Water (5 ml, 90%) collected in the trap during this time. The oil remaining, after removal of solvent and unreacted ketone in a rotary evaporator, dissolved in light petroleum (b.p. 40°/60°, 200 ml) was passed through a short column of silica gel (20×2.5 cm). Removal of solvent from the eluate gave an oil (55 g; 90%). Redistillation yielded the product as a colourless oil b.p. 114°–116°/4.5 mm.

(b) Spiro (1,3-benzodioxole-2,1'-cyclohexane): In a similar manner catechol (33 g), cyclohexanone (29.4 g, 1 equivalent) and p-toluenesulphonic acid (10 mg) were heated under reflux in toluene (300 ml) for 24 hours. Water (5 ml, 90%) collected in the trap during this time. Removal of solvent from the eluate, obtained as previously described, gave an oil (51 g, 89%). Redistillation gave a viscous liquid, b.p. 115°–116°/3.5 mm, which solidified on standing. Recrystallization from light petroleum gave the product as needles, m.p. 46°–48° (Lit. m.p. 41°).

(c) 2-Methyl-2-phenyl-1,3-benzodioxole: In the same manner catechol (33 g); acetophenone (36 g, 1 equivalent) and p-toluenesulphonic acid (10 mg) were heated under reflux in xylene (300 ml) for 5 days. Water (4.5 ml, 83%) collected in the trap. Removal of solvent from the light petroleum eluate left a yellow oil (48 g, 76%). Redistillation gave the product as a colourless oil b.p. 122°–124°/1 mm.

(d) 2,2-Dimethyl-1,3-benzoidioxole: Catechol (55 g); acetone (150 ml, excess), p-toluenesulphonic acid (10 mg) and benzene (150 ml) were heated under reflux for 48 hours. The condensed azeotrope was percolated through a bed (15 cm×2.5 cm) of molecular sieves (Union Carbide type SA, ⅛ pellets) before returning solvent/acetone to the flask. Solvents were removed in a rotary evaporator and the reaction mixture dissolved in light petroleum (200 ml). Some residual catechol which crystallized was removed by filtration and the filtrate passed through the silica-gel column. Removal of solvent from the eluate gave an oil (52 g, 70%). Redistillation gave a liquid b.p. 50°–51°/2.5 mm, b.p. 78.5°/20 mm.

(e) 2,2'-Dimethyl-2,2'-methylenebisbenzo-1,3-dioxole: Catechol (55 g, 0.5M), acetylacetone (25 g, 0.25M), p-toluenesulphonic acid (10 mg) and toluene (300 ml) were refluxed for 48 hours. Water (7.3 ml, 81%) collected in the trap. After removal of solvent and passage through silica gel in the usual manner a crystalline solid was obtained—42.5 g (70%). Recrystallized from light petroleum, needles m.p. 66°–68°.

(f) 2-Methyl-1,3-benzodioxole: Catechol (44 g) and p-toluenesulphonic acid (10 mg) in benzene (200 ml) was heated under reflux and paraldehyde (100 ml, excess) was added in 10 ml aliquots over a period of 5 days. After removal of solvent in a rotary evaporator the reaction mixture was diluted with light petroleum (200 ml), and catechol which crystallized was removed by filtration. The filtrate was passed through a column of alumina (Grade I, 20×2.5 cm). Removal of solvent left an oil (19 g, 35%), redistilled to give a colourless oil, b.p. 54°-55°/5 mm.

(g) 2-p-Methoxyphenyl-1,3-benzodioxole: Catechol (33 g), p-methoxybenzaldehyde (40.8 g, 1 equivalent) and p-toluenesulphonic acid (10 mg) in toluene (250 ml) was heated under reflux for 12 hours. Water (4 ml 74%) was collected. The cooled reaction mixture was extracted with 10% sodium hydroxide (2×50 ml), washed with water (50 ml) and dried (Na2SO4). Solvent was removed to leave an oil (37 g, 54%). Redistillation gave an oil, b.p. 172°/2.5 mm which solidified on standing, and was recrystallized from light petroleum to yield colourless needles, m.p. 59°-60°.

Tables 1 and 2 give details of benzodioxoles synthesized by the above processes.

TABLE 2

2-Substituted-1,3-benzodioxoles[a] 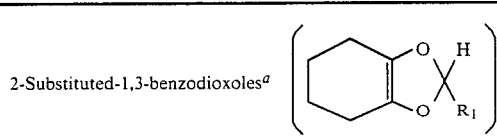

| R1 | Solvent | Reaction time | bp or mp | yield % |
|---|---|---|---|---|
| —CH3 | Benzene | 5 days | 54–55°/5 mm | 35 |
| —CH2CH3 | " | 48 hours | 54–56°/1.5 mm | 43 |
| —(CH2)2CH3 | Tolene | 48 hours | 75–80°/3.5 mm | 70 |
| —CH(CH3)2 | " | 24 hours | 203–205°/760 mm | 72 |
| —(CH2)4CH3 | " | 18 hours | 92–95°/1.5 mm | 60 |
| —C6H5 | " | 48 hours | 140°/3 mm mp 54–56° | 80 |
| —C6H4—CH3 (p-tolyl) | " | 24 hours | 148–150°/2.5 mm | 68 |
| —C6H4—OCH3 (p-methoxyphenyl) | " | 12 hours | 172°/2.5 mm mp 59–60° | 66 |
| —C6H4(o-OCH3) | " | 12 hours | 172°/2.5 mm mp 52–53° | 50 |

[a]All compounds listed in the table were shown by gas liquid chromatography to be >99% pure and had satisfactory elemental analysis.

When the substituted benzodioxole is reacted with lead tetra-acetate a variety of reaction products are formed which include acetoxy- and oxo-substituted

TABLE 1

2,2-Disubstituted-1,3-benzodioxoles[a] 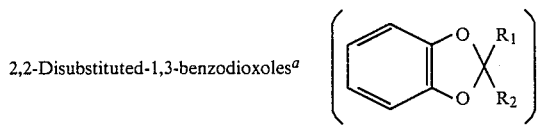

| | R1 | R2 | Solvent | Reaction time hrs | bp or mp | Yield % |
|---|---|---|---|---|---|---|
| (h) | —CH3 | —CH3 | Benzene | 36 | 50–51°/2.5 mm | 70 |
| (g) | —CH3 | —CH2CH3 | " | 72 | 64–65°/2.5 mm | 83 |
| (g) | —CH3 | —(CH2)2CH3 | " | 24 | 76–77°/2.5 mm | 68 |
| (k) | —CH3 | —CH(CH3)2 | " | 24 | 71–72°/2.5 mm | 61 |
| (l) | —CH3 | —(CH2)3CH3 | Toluene | 12 | 84–86°/1.5 mm | 73 |
| (m) | —CH3 | —CH2—CH(CH3)2 | " | 24 | 96–97°/5.0 mm | 63 |
| (n) | —CH3 | —(CH2)4CH3 | " | 10 | 114–116°/4.5 mm | 90 |
| (o) | —CH3 | —(CH2)2CH(CH3)2 | " | 24 | 110–111°/4.5 mm | 79 |
| (p) | —CH3 | —(CH2)5CH3 | " | 12 | 100–101°/1.0 mm | 85 |
| (q) | —CH3 | —(CH2)6CH3 | " | 24 | 134–135°/2.0 mm | 75 |
| (r) | —CH3 | —(CH2)7CH3 | " | 24 | 130–132°/1.5 mm | 75 |
| (s) | —CH3 | —(CH2)8CH3 | " | 24 | 139–140°/1.0 mm | 88 |
| (t) | —CH3 | —(CH2)9CH3 | " | 24 | 155–160°/1.0 mm | 78 |
| (u) | —CH3 | —(CH2)10CH3 | " | 48 | 166–168°/1.5 mm | 80 |
| (v) | —(CH2)4— | | " | 8 | 114–115°/4.5 mm | 72 |
| (w) | —(CH2)5— | | " | 24 | 115–116°/3.5 mm mp 45–48° | 90 |
| (x) | —(CH2)6— | | " | 24 | mp 55–57° | 87 |
| (y) | —CH3 | —CH2COOC2H5 | " | 72 | 130–132°/5.0 mm | 67 |
| (z) | —CH3 | (bis-benzodioxole structure) | " | 48 | mp 66–68° | 60 |
| (aa) | —CH3 | —C6H5 | Xylene | 5 days | 122–124°/1.0 mm | 76 |
| (bb) | —C6H5 | —C6H5 | " | 5 days | mp 85–87° | 60 |

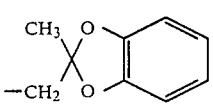

[a]All compounds listed in this table were shown by gas liquid chromatography to be >99% pure, and had satisfactory elemental analysis.

compounds which can be separated by column chromatography. The most easily recovered are the 5-acetoxy substituted and the 5,6-dione substituted benzodioxoles. The acetoxy-substituted compounds are most easily converted to the desired hydroxy-substituted compounds by alkaline hydrolysis followed by reacidification. The dione compound is best converted to the desired hydroxy compound by reduction with lithium aluminum hydride.

The following examples illustrate the second stage of the method according to the present invention wherein hydroxy groups are introduced into the benzene ring as illustrated by the following diagrammatic representations:

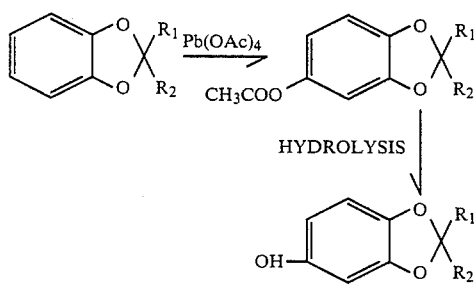

wherein $R_1$ and $R_2$ have the meanings given above.

EXAMPLE II

General Methods.

The general procedures used have been described in Part I. All starting materials had a high degree of purity (99% by g.l.c.) and had satisfactory elemental analyses and spectroscopic properties.

Oxidation of benzodioxoles by lead tetra-acetate (a) Oxidation of 2-ethyl-2-methyl-1,3-benzodioxole The benzodioxide (8.2 g–0.05 mole) and lead tetra-acetate (44.3 g–0.1 mole) were stirred in acetic acid (100 ml) at 80° for 12 hours. Residual acetic acid was removed by evaporation under reduced pressure (rotary) and the residue was partitioned between water (100 ml) and ethyl acetate (2×100 ml). The ethyl acetate extract was washed with water (50 ml) and concentrated to an oil (~8 g) which was applied to a column of t.l.c. grade silica gel (Merck Kieselgel 60) (15×4.5 cm) previously packed as a slurry in light petroleum. This column was eluted with petrol (500 ml) and petrol+1% ether (600 ml). The starting material (3.3 g) was eluted in the first petroleum fraction, followed by the product which was eluted by the 1% ether:

5-Acetoxy-2-ethyl-2-methyl-1,3-benzodioxole (2.7 g), which was obtained as a colourless oil, b.p. 120°/2 mm.

The acetate (1.0 g–4.5 m moles) in methanol (5 ml) was mixed with KOH (1.1 g–20 m moles) in water (5 ml) and the mixture left at 20° for 2 hours., Dilution with H$_2$O to 50 ml was followed by acidification and extraction with ethyl acetate (2×20 ml). The extract was washed with H$_2$O (10 ml) and was concentrated to yield the product 5-hydroxy-2-ethyl-2-methyl-1,3-benzodioxole as a colourless viscous oil (0.8 g, 100%).

(b) Oxidation of 2-butyl-2-methyl-1,3-benzodioxole

The title compound (9.6 g–0.05 mole) was oxidized as described above and the reaction mixture was resolved in a similar manner to yield, after elution of starting material (3.3 g), the following products.

5-Acetoxy-2-butyl-2-methyl-1,3-benzodioxole (3.2 g) clear oil purified by distillation, bp 146°/4 mm. The acetate (1.0 g–4 m mole) was hydrolyzed in the usual way to give 5-hydroxy-2-butyl-2-methyl-1,3-benzodioxole (0.83 g, 100%), a colourless viscous oil.

(c) Oxidation of 2-heptyl-2-methyl-1,3-benzodioxole

The title compound (11.7 g–0.05 mole) was oxidized in the usual way and the reaction mixture was resolved chromatographically as previously described. Residual starting material (4.7 g) was first obtained from the column followed in order by the products.

5-Acetoxy-2-heptyl-2-methyl-1,3-benzodioxole (3.9 g), colourless oil purified by distillation, bp 176/3 mm, The acetate (1.0 g–3.4 m mole) was hydrolyzed in the usual way to give 5-hydroxy-2-heptyl-2-methyl-1,3-benzodioxole (0.85 g, 100%) a colourless viscous oil.

(d) Oxidation of 2-methyl-2-nonyl-1,3-benzodioxole

The title compound (13.1 g–0.05 mole) was oxidized in the usual way and the reaction mixture chromatographed as described above. After recovery of unreacted starting material (5.9 g) the following products were isolated.

5-Acetoxy-2-methyl-2-nonyl-1,3-benzodioxole (5.0 g), colourless oil purified by distillation, bp 205°/2.5 mm,.

The acetate (1.0 g–3.1 m mole) was hydrolyzed in the usual way to give 5-hydroxy-2-methyl-2-nonyl-1,3-benzodioxole (0.86 g, 100%), a colourless viscous oil.

(e) Oxidation of 2-methyl-2-undecyl-1,3-benzodioxole

The title compound (14.5 g, 0.05 mole) was oxidized as previously described and the mixture was resolved on a column to give, starting material (6.0 g) and the following products.

5-Acetoxy-2-methyl-2-undecyl-1,3-benzodioxole (5.3 g), colourless oil.

The acetate (1.0 g–2.9 m mole) was hydrolyzed in the usual way to give 5-hydroxy-2-methyl-2-undecyl-1,3-benzodioxole (0.87 g, 100 %), a colourless viscous oil.

(f) Oxidation of spiro 1,3-benzodioxole-2,1'-cycloheptane

The title compound (4.08 g–0.02 mole) was oxidized in the usual manner. Separation of the reaction mixture was achieved on a chromatographic column and gave starting material (2.4 g) and the following product.

5-Acetoxy-spiro (1,3-benzodioxole-2,1'-cycloheptane) (1.2 g), colourless oil which solidified on standing, plates from petrol, mp 36°–38°.

The acetate (1.0 g–3.8 m moles) was hydrolyzed to give 5-hydroxy-spiro (1,3-benzodioxole-2,1'-cycloheptane) (0.84 g, 100%), colourless crystals, mp 80°–82°.

(g) Oxidation of 2-methyl-2-phenyl-1,3-benzodioxole

The tile compound (10.6 g–0.05 mole) was oxidized in the usual way, and products were recovered from a chromatographic column. Residual starting material (6.0 g) eluted first followed by products.

5-Acetoxy-2-methyl-2-phenyl-1,3-benzodioxole (2.5 g), obtained as colourless needles from methanol, mp 87°–87.5°.

The acetate (1.0 g–4 m mole) was hydrolyzed as before to give 5-hydroxy-2-methyl-2-phenyl-1,3-benzodioxole (0.82 g, 100%), colourless crystals mp 94.5°–95.5°.

(h) Oxidation of 2,2-diphenyl-1,3-benzodioxole

The title compound (13.7 g–0.05 mole) was oxidized in the usual way. Chromatographic separation on a column gave first the unreacted starting material (6 g) followed by:

5-Acetoxy-2,2-diphenyl-1,3-benzodioxole (1.9 g), obtained as colourless needles from methanol, mp 81.5°–82.5°.

The acetate (1.0 g–3.0 m moles) was hydrolyzed as before to give 5-hydroxy-2,2-diphenyl-1,3-benzodioxole (0.87 g, 100%), colourless crystals mp 138.5°–140.5°.

TABLE 3

Preparation of 5-hydroxy-2,2-disubstituted-1, 3-benzodioxoles from the corresponding 5-acetoxy compounds.

| $R_1$ | $R_2$ | Yield (%) | mp. |
|---|---|---|---|
| —$CH_3$ | —$C_2H_5$ | 100 | liq. |
| —$CH_3$ | —$C_4H_9$ | " | " |
| —$CH_3$ | —$C_7H_{15}$ | " | " |
| —$CH_3$ | —$C_9H_{19}$ | " | " |
| —$CH_3$ | —$C_{11}H_{23}$ | " | " |
| —$(CH_2)_5$— | | " | 68–69° |
| —$(CH_2)_6$— | | " | 94–95° |
| —$CH_3$ | —$C_6H_5$ | " | 94–95.5° |
| —$C_6H_5$ | —$C_6H_5$ | " | 138.5–140.5° |

(r) Example of the preparation of a dihydroxy benzodioxole

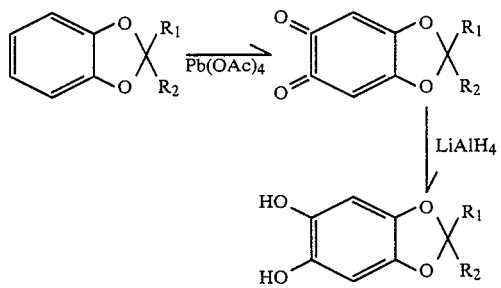

Spiro (1,3-benzodioxole-2,1'-cyclohexanol (9.5 g–0.05 mole) was oxidized by lead tetra-acetate (44.3 g–0.1 mole) in acetic acid at 80° for 10 hrs. After the usual work up the reaction mixture was separated on a silica-gel column. Spiro (1,3-benzodioxole-2,1'-cyclohexane)-5,6-dione was one of the pure products obtained. Yellow needles mp 186°–187°.

The above quinone (1 g–4.5 m mole) in dry ether (300 ml), was refluxed with lithium aluminium hydride (0.6 g–excess) for 2 hrs. Excess reagent was decomposed by addition of ethyl acetate, and the mixture was then added to water (200 ml) acidified with HCl. The product, 5,6-dihydroxy spiro (1,3 benzodioxole-2,1'cyclohexane) was obtained from the ether layer in the usual way and formed colourless plates (0.08 g–78%) mp 136°–138°.

The following example is given to illustrate the effectiveness of the compounds according to this invention as antioxidants as compared with conventional food grade antioxidants.

EXAMPLE 3

All glasswares were cleaned thoroughly, kept in 50% nitric acid, rinsed with distilled water and dried before use. Lard was freshly prepared immediately before use. All samples were stored under vacuum in the dark.

Purification of Lard.

Lard obtained from Woolworth store (Allowrie) was dissolved in A.R. light petroleum (40° C.–60° C.) 100 g lard 300 ml Pet. ether) and the mixture was passed through a column of alumina which was activated at 600° C./4 hrs before use (Approx. 50 g alumina in a column 3×30 cm), under a nitrogen atmosphere. Solvent was removed using a rotary evaporator and trace amounts of solvent were removed under high vacuum at 70° C. for 12 hours. The purity of purified lard was checked using peroxide value and the IR spectrum.

Preparation of Samples.

Except for propyl gallate all antioxidants were dissolved in lard at the concentration of 1% (molecularly equivalent to 1% BHA) and this stock solution was diluted to 0.01%. Propyl Gallate was not very soluble in lard, thus a 0.25% stock solution was prepared. During the preparation step, lard was warmed up to 35°–40° C. to liquify under a nitrogen atmosphere. All samples including the stock solutions were prepared immediately before use. Three tests were carried out, each test was done in triplicate.

Antioxidant test was weight gain method (Olcott H. S. and Einset, E. J. JAOCS 35 161 (1958). Test samples (1 g) were put in beakers (40 mls, 4 cm diameter) which are placed in a convection type oven kept at 60° C. At daily intervals the beakers were removed, allowed to cool for 15 mins and weighed with a semi-micro balance (Bosch, S2000). The end of the induction period was taken at the day closest to the day of 0.4% increase in weight.

All reference antioxidants were obtained commercially.

Sesamol from Aldrich Chemical Company, U.S.A.
BHA from May & Baker Ltd., England
Propyl Gallate from Koch-Light Lab. Ltd., England The 2-hydroxy-1,3-benzodioxoles were products of alkaline hydrolysis of 2-acetoxyl-1,3-benzodioxoles obtained from lead tetraacetate oxidation of 1,3 benzodioxoles.

The results obtained are shown graphically in FIG. 1.

The results presented in FIG. 1, clearly demonstrate that whereas the control sample, viz. lard without the presence of any antioxidant, begins to gain weight due to oxidation on day 1, the prior art antioxidants BHA, sesamol and PG retard oxidation only until days 55, 62 and 67, respectively. In contrast, the antioxidants of the present invention designated 4 to 12 in said FIG. 1 and having the formulae shown in FIG. 1, show remarkably improved result by retarding the oxidation from at least 77 days to about 100 days.

We claim:

1. A method of retarding oxidation of foodstuffs containing edible oils or fats, comprising, mixing with a foodstuff an antioxidation effective amount of a benzodioxole compound having the structure

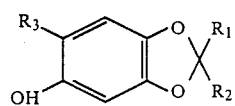

wherein
$R_1$ is a hydrogen atom or an alkyl group or an aryl group;
$R_2$ is an alkyl group or an aryl group;
or
$R_1$ and $R_2$ together form a cycloalkyl group; and
$R_3$ is a hydrogen atom or an hydroxyl group.

2. The method of retarding oxidation according to claim 1, wherein said foodstuff comprises an edible oil.

3. The method of retarding oxidation according to claim 1, wherein the effective amount of said benzodioxole compound is 0.1% to 0.001% by weight.

4. The method of retarding oxidation according to claim 1, wherein $R_1$ is $CH_3$, $R_2$ is $C_2H_5$ and $R_3$ is H.

5. The method of retarding oxidation according to claim 1, wherein $R_1$ is $CH_3$, $R_2$ is $C_4H_9$ and $R_3$ is H.

6. The method of retarding oxidation according to claim 1, wherein $R_1$ is $CH_3$, $R_2$ is $C_7H_{15}$ and $R_3$ is H.

7. The method of retarding oxidation according to claim 1, wherein $R_1$ is $CH_3$, $R_2$ is $C_9H_{19}$ and $R_3$ is H.

8. The method of retarding oxidation according to claim 1, wherein $R_1$ is $CH_3$, $R_2$ is $C_{11}H_{21}$ and $R_3$ is H.

9. The method of retarding oxidation according to claim 1, wherein $R_1$ and $R_2$ each comprises a phenyl radical and $R_3$ is H.

* * * * *